United States Patent [19]

Isak et al.

[11] Patent Number: 5,446,199

[45] Date of Patent: Aug. 29, 1995

[54] PREPARATION OF HALOMETHYLBENZOYL CYANIDES AND NOVEL HALOMETHYLBENZOYL CYANIDES

[75] Inventors: Heinz Isak, Boehl-Iggelheim; Thomas Wettling, Limburgerhof; Michael Keil, Freinsheim; Bernd Wolf, Fussgoenheim; Reinhard Doetzer, Weinheim, all of Germany

[73] Assignee: BASF Aktiengesellschaft, Ludwigshafen, Germany

[21] Appl. No.: 216,416

[22] Filed: Mar. 23, 1994

[30] Foreign Application Priority Data

Apr. 8, 1993 [DE] Germany .................. 43 11 722.8

[51] Int. Cl.$^6$ .......................................... C07C 253/14
[52] U.S. Cl. ................................................ 562/869
[58] Field of Search ........................................ 562/869

[56] References Cited

U.S. PATENT DOCUMENTS

Re. 33,989  7/1992  Wenderoth et al. .
5,221,762  6/1993  Wingent et al. .

FOREIGN PATENT DOCUMENTS 0254426  1/1988  European Pat. Off. .
334720  9/1989  European Pat. Off. .
0352543  1/1990  European Pat. Off. .
398783  11/1990  European Pat. Off. .
1813184  8/1969  Germany .
2835440  2/1980  Germany .

OTHER PUBLICATIONS

Chemical Reviews, vol. 69, No. 1, Feb. 1969, A. J. Parker, "Protic–Dipolar Aprotic Solvent Effects on Rates of Bimolecular Reactions", pp. 1–30.
J. Am. Chem. Soc., vol. 68, 1946, pp. 2741–2742, S. Wawzonek, et al., "The Action of Cuprous Cyanide on p–Methoxybenzyl Chloride".
Houben–Weyl, Methoden der Organischen Chemie (Methods of Organic Chemistry), vol. VIII, 4th edition, Georg Thieme Verlag, Stuttgart 1952, p. 294.

Chem. Ber., vol. 31, (1898), pp. 1023–1024.
Org. Synthesis, vol. 24, 1944, pp. 14–16, T. S. Oakwood, et al., "Benzoyl Cyanide".
Liebigs' Annalen der Chemie, vol. 287, 1895, p. 307.
Annalen der Chemie, vol. 3, (1832), pp. 249,267–268, F. Wohler, et al., "Untersuchungen Über das Radikal der Benzoesaure".

*Primary Examiner*—Paul J. Killos
*Attorney, Agent, or Firm*—Oblon, Spivak, McClelland, Maier & Neustadt

[57] ABSTRACT

A process for preparing halomethylbenzoyl cyanides I

Ph-CO-CN        I (Ph=phenyl radical substituted by chloromethyl or bromomethyl which, if desired, can additionally carry 1–4 further radicals) by reacting halomethylbenzoyl chlorides II Ph-CO-Cl        II with an alkali metal cyanide or transition metal cyanide, if appropriate in an organic diluent, and novel halomethylbenzoyl cyanides I'

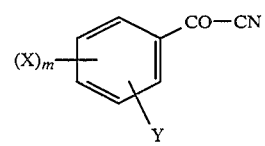

(X=halogen, $C_1$–$C_4$-alkyl, $C_1$–$C_4$-alkoxy, $CF_3$, $C_1$–$C_5$-alkyl-($C_1$–$C_5$-alkyl)hydroxyimino or $C_1$–$C_5$-alkyl-($C_2$–$C_5$-alkenyl)hydroxyimino; m=0 to 4 and Y=-chloromethyl or bromomethyl) are described.

The halomethylbenzoyl cyanides I are important intermediates for the synthesis of plant protection agents.

4 Claims, No Drawings

PREPARATION OF HALOMETHYLBENZOYL CYANIDES AND NOVEL HALOMETHYLBENZOYL CYANIDES

DESCRIPTION

The present invention relates to a process for preparing halomethylbenzoyl cyanides of the general formula I Ph-CO-CN     I where Ph is a phenyl radical which is substituted by chloromethyl or bromomethyl and which, if desired, can additionally carry 1 to 4 further radicals which are inert to the reaction.

It is generally known that benzoyl cyanide can be prepared, inter alia, by reacting benzoyl chloride
- with mercuric cyanide (F. Wöhler and J. Liebig, Annalen der Chemie 3, (1832) 249, 267),
- with silver cyanide (Liebigs' Annalen der Chemie 287, (1895) 307),
- with dry copper(I) cyanide (Org. Synthesis 24, (1944) 14) or
- with dry hydrogen cyanide in the presence of pyridine (Chem. Ber. 31, (1898) 1023).

In EP-A 352 543, substituted benzoyl cyanides (see formula II on page 4 of the description and claim 5) are mentioned, inter alia, as possible starting materials for herbicidal 4-phenylpyrazoles (see reaction scheme (4) on page 10 of the description). A method for preparing these benzoyl cyanides is not given, however. Apart from a general formula for the benzoyl cyanides, not even one individual compound is disclosed.

DE-A 40 42 282 discloses the preparation of 2-phenoxymethylbenzoyl cyanides by reaction of 2-phenoxymethylbenzoyl chlorides with alkali metal cyanides or alkaline earth metal cyanides, if desired in the presence of hydrocyanic acid. This process, however, appears to be unsuitable for the preparation of the halomethylbenzoyl cyanides I, as according to Houben-Weyl, Methoden der Organischen Chemie (Methods of Organic Chemistry), volume VIII, 4th edition, Georg Thieme Verlag, Stuttgart 1952, p. 294, an α-haloalkyl side chain on an aromatic reacts very easily with alkali metal cyanides. The reaction of benzyl chloride with sodium cyanide is given by way of example on this point. The reaction of benzyl chloride with copper(I) cyanide at 150° .C with the exclusion of water, which is known from J. Am. Chem. Soc. 68, (1946) 2741, is additionally referred to.

In a similar manner to the method known from Houben-Weyl, in the reaction of the halomethylbenzoyl chlorides II with alkali metal cyanides or transition metal cyanides a product mixture of cyanomethylbenzoyl chloride and halomethylbenzoyl cyanide would accordingly be expected.

It is an object of the present invention to make available an industrially utilizable process for preparing the compound I.

We have found that this object is achieved by the present process for preparing halomethylbenzoyl cyanides, which comprises reacting a halomethylbenzoyl chloride of the formula II Ph-CO-Cl     II with an alkali metal cyanide or transition metal cyanide.

The halomethylbenzoyl chlorides II can be prepared by known halogenation methods from the corresponding methyl-substituted benzene derivatives (cf. e.g. DE-A 28 35 440) or from the corresponding benzoic acids (cf. e.g. DE-A 40 42 282):

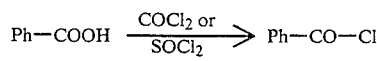

The process according to the invention is normally carried out at atmospheric pressure or at slightly reduced pressure, a reaction temperature of from (−20°) to 100° C., preferably from 0° to 80° C., in particular from 20° to 80° C., being recommended.

Among the alkali metal cyanides, sodium cyanide and potassium cyanide are preferred. Among the transition metal cyanides, those suitable are, for example, mercury(I) cyanide, silver cyanide and preferably copper(I) cyanide.

In general, the halomethylbenzoyl chloride II and the alkali metal cyanide or transition metal cyanide are employed in approximately stoichiometric amounts. However, an excess of cyanide up to a two-fold amount is preferred, in particular from a 1.05- to 1.5-fold amount, based on the amount of II.

If the halomethylbenzoyl chloride II employed is not present in liquid form, the addition of an inert organic solvent or diluent is advisable, aprotic dipolar and non-polar solvents being particularly suitable.

Aprotic dipolar solvents are to be understood as meaning those solvents in which a solvent molecule has a marked dipole moment, but bears no hydrogen atoms which are capable of the formation of hydrogen bridges. The dielectric constant of such solvents is greater than 15. Reference may be made to A. J. Parker, Chem. Rev. 69 (1969), pages 1–32, in particular page 2, with respect to the definition of aprotic dipolar solvents.

Suitable aprotic dipolar solvents are, for example, sulfoxides such as dimethyl sulfoxide, diethyl sulfoxide, dimethyl sulfone, diethyl sulfone, methyl ethyl sulfone and tetramethylene sulfone; nitriles such as acetonitrile, benzonitrile, butyronitrile, iso-butyronitrile and m-chlorobenzonitrile; N,N-dialkyl-substituted carboxamides such as dimethylformamide, tetramethylurea, N,N-dimethylbenzamide, N,N-dimethylacetamide, N,N-dimethylphenylacetamide, N,N-dimethylcyclohexanecarboxamide, N,N-dimethylpropionamide and homologous carboxylic acid piperidide, carboxylic acid morpholide and carboxylic acid pyrrolidide, the corresponding N,N-diethyl-, N,N-dipropyl-, N,N-diisopropyl-, N,N-diisobutyl-, N,N-dibenzyl-, N,N-diphenyl-, N-methyl-N-phenyl-, N-cyclohexyl-N-methyl and N-ethyl-N-tert-butyl compounds of the abovementioned N,N-dimethyl compounds, in addition N-methylformanilide, N-ethylpyrrolidone, N-butylpyrrolidone, N-ethyl-4-piperidone, N-methylpyrrolidone and hexamethylphosphoramide. Mixtures of the solvents mentioned are also suitable.

Those preferred are dimethylacetamide, N-methylpyrrolidone, dimethylformamide, dimethyl sulfoxide, tetramethylene sulfone, acetone and acetonitrile.

Suitable non-polar solvents are preferably aromatic hydrocarbons such as benzene, toluene and o-, m- or p-xylene, chlorinated hydrocarbons such as dichloromethane and alcohols such as methanol and ethanol. Toluene is particularly preferred.

The course of the process can be favorably affected by adding a catalyst. Normally, the 0.005- to 2-fold amount, in particular the 0.01- to 0.5-fold amount, of catalyst is adequate, based on the amount of II.

Suitable catalysts for this purpose are generally the halides, cyanides, hydroxides, hydrogensulfates, $C_1$-$C_4$-alkylsulfates and tetrafluoroborates of quaternary nitrogen compounds and aryl- and alkylphosphonium halides, for example tetra-($C_1$-$C_4$-alkyl)ammonium halides such as tetraethylammonium chloride, tetraethylammonium bromide, tetrapropylammonium bromide, tetrabutylammonium chloride, tetrabutylammonium bromide, tetrabutylammonium iodide, tetraoctylammonium bromide, tributylmethylammonium chloride, hexadecyltrimethylammonium bromide, hexadecyltrimethylammonium chloride solution, ethylhexadecyldimethylammonium bromide, methyltrioctylammonium chloride, the salts of the following ammonium, piperidinium and morpholinium ions with ethylsulfate or bromide as oppositely charged ions: cyclohexyldiethyl-n-butylammonium, $C_1$-$C_6$-alkylbenzyldimethylammonium chlorides, benzyltributylammonium bromide, benzyltributylammonium chloride, benzyltriethylammonium chloride, benzyltrimethylammonium chloride, benzylcyclohexyldiethylammonium, benzyl-di-n-propylethylammonium, benzyl-di-n-butylethylammonium, benzylbutylcyclohexylethylammonium, butyl-di(methoxyethyl)ethylammonium, benzyldimethoxyethylethylammonium, dibenzyl-di-n-propylammonium, dibenzyl-di-n-butylammonium, di-n-butyl-di(methoxyethyl)ammonium, benzyl-n-butyl-di(methoxyethyl)ammonium, dibenzyl-di(methoxyethyl)ammonium, N-(n-butyl)-N-ethylpiperidinium, N-benzyl-N-ethylpiperidinium, 4-(n-butyl)-4-ethylmorpholinium, 4-benzyl-4-ethylmorpholinium, N-di(n-butyl)piperidinium, N-benzyl-N-(n-butyl)piperidinium, 4-di(n-butyl)morpholinium, 4-benzyl-4-(n-butyl)morpholinium, cyclohexyldibenzylethylammonium, N,N-di(n-butyl)hexamethyleneiminium, N-benzyl-N-(n-butyl)hexamethyleneiminium, N,N-dibenzylhexamethyleneiminium, N,N-dibenzylpiperidinium, 4,4-dimethylmorpholinium, N,N-di(n-butyl)pyrrolidinium, N-benzyl-N-(n-butyl)pyrrolidinium, N,N-dibenzylpyrrolidinium, N-benzyl-N-hexylpiperidinium, N-benzyl-N-(2-methylpentyl)-piperidinium, N-benzyl-N-(2-ethylhexyl)-piperidinium, 1,1-di(n-butyl)-2-ethylpiperidine, 1-benzyl-1-(n-butyl)-2-ethylpiperidine, 4-benzyl-4-hexylmorpholinium, 4-(n-butyl)-4-hexylmorpholinium, 4-benzyl-4-(2-ethylhexyl)morpholinium, N-(n-butyl)-N-isobutylhexamethyleneimine, N-benzyl-N-isobutylhexamethyleneimine, N-isoamyl-N-benzylhexamethyleneimine, N-benzyl-N-(n-butyl)-3,3,5-trimethylhexamethyleneimine, N-benzyl-N-(2-methylbutyl)piperidinium, N-benzyl-N-(3-methylbutyl)piperidinium, N-benzyl-N-(2-methyl-3-methylbutyl)piperidinium, N-cyclopentylpiperidinium, N-benzyl-N-(2-methyl-3-ethoxypropyl)piperidinium, cyclohexyldiethyl-(n-butyl)ammonium, 4-benzyl-4-(2-methylamyl)morpholinyl, 1-benzyl-1-(n-butyl)-2-(n-butyl)-2-ethyl-piperidinium, N-benzyl-N-ethylhexamethyleneiminium, N-benzyl-N-(2-methylamyl)hexamethyleneiminium, N-benzyl-N-(3,5-dimethyl-5-methylhexyl)hexamethyleneiminium, N-benzyl-N-(2-methylamyl)-3,3,5-trimethylhexamethyleneiminium, N-benzyl-N-(2-ethylhexyl)-3,3,5-trimethylhexamethylene iminium, N-benzyl-N-cyclohexylhexamethyleneiminium, N-benzyl-N-(2-methyl-2-methoxyethyl)hexamethyleneiminium, N-benzyl-N-(2-methyl-2-n-butoxyethyl)hexamethyleneiminium, N-benzyl-N-[2-methyl-2-(2-methoxyethoxy)ethyl]hexamethyleneim inium, N-benzyl-N-(2,5-dimethyl-2-propoxyethyl)hexamethyleneiminium, N-benzyl-N-(2-methyl-3-methylbutyl)-3,3,5-trimethylhexamethyl eneiminium, N-benzyl-N-(tetrahydropyran-2-ylmethyl)-piperidinium, N-benzyl-N-(2-methyl-2-methoxyethyl)piperidinium, N-benzyl-N-(2-methyl-2-n-butoxyethyl)piperidinium, N-benzyl-N-[2-methyl-2-(2-methoxyethoxy)ethyl]piperidinium, N-benzyl-N-(4,4-dimethylamyl)piperidinium, N-benzyl-N-(tetrahydropyran-2-ylmethyl)hexamethyleneiminium, N-benzyl-N-(2-methyl-3-methylbutyl)hexamethyleneiminium, N-benzyl-N-(2-methyl-3-methylbutyl)pyrrolidinium, 4-benzyl-4-(2-methyl-3-methylbutyl)morpholinium, N-benzyl-N-(n-propyl)hexamethyleneiminium, N-benzyl-N-(isopropyl)hexamethyleneiminium, n-butyl-(2-methylbutyl)-di(2-methoxyethyl)ammonium, benzyl-(2-methylbutyl)-di(2-methoxyethyl)ammonium, (bis-ethylbutylbenzylammonium)hexane, n-butyl-(3-methylbutyl)-di(2-methoxyethyl)ammonium, N-benzyl-(3-methylbutyl)-di(2-methoxyethyl)ammonium, 1,ω-di-(N-ethyl-hexamethyleneiminium)hexyl,1,ω-di-(N-benzylhexamethyleneiminium)hexyl, 1,ω-di-(N-n-butylhexamethyleneiminium)hexyl, 1,ω-di-(N-ethylhexamethyleneiminium)octyl, 1,ω-di-(N-benzylhexamethyleneiminium)octyl, 1,ω-di-(N-n-butylhexamethyleneiminium)octyl, 1,ω-di-(N-ethylpiperidinium)hexyl, 1,ω-di-(N-benzylpiperidinium)hexyl, 1,ω-di-(N-n-butylpiperidinium)hexyl,1,ω-di-(N-ethylpiperidinium)octyl, 1,ω-di-(N-benzylpiperidinium)octyl, 1,ω-di-(N-n-butylpiperidinium)octyl, 1,ω-di-(N-ethylpyrrolidinium)hexyl, 1,ω-di-(N-benzylpyrrolidinium)hexyl, 1,ω-di-(N-n-butylpyrrolidinium)hexyl, 1,ω-di-(N-ethylpyrrolidinium)octyl, 1,ω-di-(N-benzylpyrrolidinium)octyl, 1,ω-di-(N-n-butylpyrrolidinium)octyl, dibutylethylphenethylammonium, n-butyl-2-methylbutyl-di-(2-methoxyethyl)ammonium, di-(2-methoxyethyl)-di-(n-propyl)ammonium , di-(2-methoxyethyl)diamylammonium, (−)-N-benzylquininium chloride and (−)-N-dodecyl-N-methylephedrinium bromide, tetra($C_1$-$C_4$-alkyl)ammoniumcyanides such as tetraethylammonium cyanide and tetrabutylammonium cyanide, and also tetraethylammonium hydroxide solution, tetrabutylammonium hydroxide solution, benzyltriethylammonium hydroxide solution, benzyltrimethylammonium hydroxide solution, benzyltrimethylammonium hydroxide solution, tetrabutylammonium fluoride trihydrate, tetrabutylammonium hydrogensulfate, tetrabutylammonium tetrafluoroborate, tetraethylammonium fluoroborate, alkyl- and aryl-substituted phosphonium halides such as ethyltrioctylphosphonium bromide, tributylhexadecylphosphonium bromide, tetrabutylphosphonium bromide, tetrabutylphosphonium chloride solution, butyltriphenylphosphonium chloride, tetraphenylphosphonium bromide and tetraphenylphosphonium chloride.

According to the findings to date, tetrabutylammonium chloride, tetrabutylammonium bromide and the tetraalkylammonium cyanides are particularly highly suitable. They are preferably employed as approximately 50% strength by weight aqueous solutions.

If the alkali metal cyanide is in aqueous solution and the halomethylbenzoyl chloride II in an organic phase, it is recommended to accelerate the reaction by adding a phase-transfer catalyst.

Particularly highly suitable phase-transfer catalysts for this purpose are crown ethers such as benzo-15-crown-5, tris[2-(2-methoxyethoxy)ethyl]amine, dicyclohexyl-18-crown-6 and 18-crown-6-tetracarboxylic acid.

The phase-transfer catalyst is expediently employed in an amount from 0.001 to 1 mol %, in particular from 0.001 to 0.08 mol %, based on the amount of II.

The process according to the invention can be carried out both batchwise and continuously. In the continuous procedure, the reaction component is passed, for example, through a tubular reactor or over stirring vessel cascades. The process products I can be purified in a customary manner, e.g. by means of distillation.

The halomethylbenzoyl cyanides I are obtained by the process according to the invention in very good purity in a technically simple manner. The 2-halomethylbenzoic acid produced as a by-product during the preparation of the 2-halomethylbenzoyl cyanides can be converted into phthalide, which can be used again for preparing II.

With respect to the desired process products I, Ph is preferably a radical

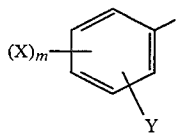

In the process products I and the novel halomethylbenzoyl cyanides of the formula I'

X is halogen, in particular fluorine or chlorine, $C_1$–$C_4$-alkyl, in particular methyl or ethyl, $C_1$–$C_4$-alkoxy, in particular methoxy, ethoxy or isopropoxy, $C_1$–$C_4$-haloalkyl, in particular trifluoromethyl, —C($C_1$–$C_5$-alkyl)=N—O—($C_1$–$C_5$-alkyl) or —C($C_1$–$C_5$-alkyl)=N—O—($C_2$–$C_5$-alkenyl), in particular methylhydroxyimino and —C(CH$_3$)=N—OCH$_3$;

m is 0 to 4, preferably 0 and

Y is chloromethyl or bromomethyl, preferably in position 2, chloromethyl being particularly preferred.

The halomethylbenzoyl cyanides I and I' are useful intermediates for preparing various plant protection agents, for example the herbicidal 4-phenylpyrazoles, as are described in EP-A 352 543.

The process products I and I' can additionally be used for the synthesis of arylglyoxylic acid esters as described in DE-A 40 42 271. The crude product mixture of phenylglyoxylic acid esters and their ketals obtained from the Pinner reaction described there can be converted without further purification as described in DE-A 40 42 272 into the E-oxime ethers of phenylglyoxylic acid esters of the formula

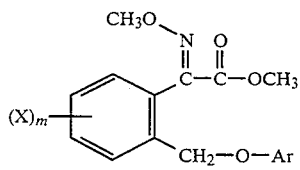

where Ar is substituted or unsubstituted phenyl. Compounds of the formula III are preferably used as fungicides, acaricides or insecticides in plant protection (cf. e.g. EP-A 253 213 and EP-A 254 426).

PREPARATION EXAMPLES

Example 1

Preparation of 2-chloromethylbenzoyl cyanide under phase-transfer conditions in water/toluene 1 g (3 mmol) of tetrabutylammonium bromide was added to a solution of 117.6 g (2.4 mol) of sodium cyanide in 400 g of water. The mixture obtained was then adjusted to a pH of 10.5 using about 200 g of 1% strength by weight hydrochloric acid, after which 1000 g of toluene were added. A solution of 378 g (2.0 mol) of 2-chloromethylbenzoyl chloride in 1000 ml of toluene was metered into this 2-phase mixture in the course of 30 min.

After stirring at 25°–35° C. for about 2–3 hours, the phases were separated. The organic phase was washed once each with 200 ml of water and 200 ml of 1% strength by weight hydrochloric acid, then dried over magnesium sulfate and concentrated. The crude product was purified by means of fractional distillation (b.p.: 100° C., 0.3 mbar). Yield: 292.34 g (82%)

Example 2

Preparation of 2-chloromethylbenzoyl cyanide in acetonitrile/water

A solution of 9.45 g (0.05 mol) of 2-chloromethylbenzoyl chloride in 100 ml of water-moist acetonitrile was treated with 4.9 g (0.1 mol) of sodium cyanide, after which the reaction mixture was stirred at approximately 25°–30° C. for 24 hours. HPLC analysis showed 19% of a mixture of phthalide and 2-chloromethylbenzoic acid, 76% of 2-chloromethylbenzoyl cyanide and 5% of dimeric benzoyl cyanide.

It was possible to separate the crude product mixture by means of chromatography on silica gel or by means of fractional distillation (see Example 1).

Yield: 6.3 g (70.5%), b.p. $_{0.3}$ = 100° C.

Example 3

Preparation of 2-chloromethylbenzoyl cyanide using CuCN

A solution of 9.45 g (0.05 mol) of 2-chloromethylbenzoyl chloride in 100 ml of acetonitrile was treated with 8.9 g (0.1 mol) of Cu(I) cyanide, after which the reaction mixture was stirred at about 0° C. for 24 hours. HPLC analysis showed 24% of phthalide, 62% of 2-chloromethylbenzoyl cyanide and about 10% of dimeric benzoyl cyanide.

It was possible to separate the reaction mixture by chromatography on silica gel (eluent: hexane/toluene = 1:1) or by fractional distillation as described in Example 1 (b.p. $_{0.5}$ = 106° C.).

Yield: 5.27 g (58%)

We claim:

1. A process for preparing halomethylbenzoyl cyanides of the formula I

Ph-CO-CN    I where Ph is a phenyl radical which is substituted by chloromethyl or bromomethyl and which, if desired, can additionally carry 1 to 4 further radicals which are inert to the reaction, which comprises reacting a halomethylbenzoyl chloride of the formula II Ph-CO-Cl    II with an aqueous alkali metal cyanide or transition metal cyanide solution in an organic diluent in the presence of a phase transfer catalyst.

2. The process of claim 1, wherein said aqueous alkali metal cyanide or transition metal cyanide is sodium cyanide or potassium cyanide.

3. The process of claim 1, wherein said halomethylbenzoyl cyanide is a halomethylbenzoyl cyanide of Formula I'

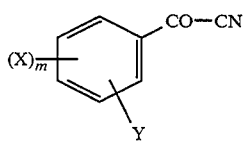

where the variables have the following meanings
X is halogen, $C_1$–$C_4$-alkyl, $C_1$–$C_4$-alkoxy, trifluoromethyl, $C_1$–$C_5$-alkyl-($C_1$–$C_5$-alkyl)hydroxyimino and $C_1$–$C_5$-alkyl-($C_2$–$C_5$-alkenyl)hydroxyimino;
m is 0 to 4 and
Y is chloromethyl or bromomethyl.

4. The process of claim 3, wherein Y is 2-chloromethyl.

* * * * *